United States Patent
Decarlo et al.

(10) Patent No.: US 9,700,370 B2
(45) Date of Patent: Jul. 11, 2017

(54) LIMITED REUSE ABLATION NEEDLES AND ABLATION DEVICES FOR USE THEREWITH

(71) Applicant: COVIDIEN LP, Mansfield, MA (US)

(72) Inventors: Arnold V. Decarlo, Frederick, CO (US); William O. Reid, Jr., Frederick, CO (US)

(73) Assignee: COVIDIEN LP, Mansfield, MA (US)

( * ) Notice: Subject to any disclaimer, the term of this patent is extended or adjusted under 35 U.S.C. 154(b) by 0 days.

(21) Appl. No.: 15/181,042

(22) Filed: Jun. 13, 2016

(65) Prior Publication Data

US 2016/0296276 A1    Oct. 13, 2016

Related U.S. Application Data

(63) Continuation of application No. 13/460,440, filed on Apr. 30, 2012, now Pat. No. 9,364,278.

(51) Int. Cl.
*A61B 18/14* (2006.01)
*A61B 17/00* (2006.01)
(Continued)

(52) U.S. Cl.
CPC .......... *A61B 18/1477* (2013.01); *A61B 18/14* (2013.01); *A61B 90/08* (2016.02);
(Continued)

(58) Field of Classification Search
CPC ................ A61B 18/14; A61B 18/1477; A61B 2017/0023; A61B 2017/00473; A61B 2017/00477; A61B 2018/00023; A61B 2018/00178; A61B 2018/0091; A61B 2018/00988; A61B 2018/1495;
(Continued)

(56) References Cited

U.S. PATENT DOCUMENTS

D223,367 S    4/1972 Kountz
D263,020 S    2/1982 Rau, III
(Continued)

FOREIGN PATENT DOCUMENTS

CN    1103807 A    6/1995
CN    101939879 A    1/2011
(Continued)

OTHER PUBLICATIONS

European Search Report EP 02786604.5 dated Feb. 10, 2010.
(Continued)

*Primary Examiner* — Amanda Patton

(57) ABSTRACT

A surgical instrument includes a reusable component and a limited-use component releasably engagable with the reusable component. The limited-use component is configured for one or more uses and includes a clocking mechanism configured to count each engagement of the reusable component and the limited-use component to one another. The clocking mechanism is incrementally transitionable upon each successive count from one or more uses state, wherein the clocking mechanism permits both mechanical engagement and electrical coupling of the reusable component and the limited-use component to one another, to a spent state, wherein the clocking mechanism inhibits both mechanical engagement and electrical coupling of the limited-use component and the reusable component to one another.

17 Claims, 7 Drawing Sheets

(51) Int. Cl.
  *A61B 18/00* (2006.01)
  *A61B 90/00* (2016.01)
(52) U.S. Cl.
  CPC ........... *A61B 2017/0023* (2013.01); *A61B 2017/00473* (2013.01); *A61B 2017/00477* (2013.01); *A61B 2018/00023* (2013.01); *A61B 2018/0091* (2013.01); *A61B 2018/00178* (2013.01); *A61B 2018/00988* (2013.01); *A61B 2018/1495* (2013.01); *A61B 2090/0803* (2016.02); *A61B 2090/0804* (2016.02); *A61B 2090/0806* (2016.02); *A61B 2090/0808* (2016.02); *A61B 2090/0814* (2016.02)
(58) Field of Classification Search
  CPC .... A61B 2018/4815; A61B 2018/4821; A61B 2018/4831; A61B 2018/4873
  See application file for complete search history.

(56) References Cited

U.S. PATENT DOCUMENTS

| | | | |
|---|---|---|---|
| D266,842 | S | 11/1982 | Villers et al. |
| D278,306 | S | 4/1985 | McIntosh |
| D295,893 | S | 5/1988 | Sharkany et al. |
| D295,894 | S | 5/1988 | Sharkany et al. |
| D354,218 | S | 1/1995 | Van de Peer |
| 5,448,042 | A | 9/1995 | Robinson et al. |
| D424,693 | S | 5/2000 | Pruter |
| D424,694 | S | 5/2000 | Tetzlaff et al. |
| D425,201 | S | 5/2000 | Tetzlaff et al. |
| 6,221,070 | B1 | 4/2001 | Tu et al. |
| D449,886 | S | 10/2001 | Tetzlaff et al. |
| D457,958 | S | 5/2002 | Dycus et al. |
| D457,959 | S | 5/2002 | Tetzlaff et al. |
| D487,039 | S | 2/2004 | Webster et al. |
| D496,997 | S | 10/2004 | Dycus et al. |
| D499,181 | S | 11/2004 | Dycus et al. |
| D525,361 | S | 7/2006 | Hushka |
| D531,311 | S | 10/2006 | Guerra et al. |
| D533,942 | S | 12/2006 | Kerr et al. |
| D535,027 | S | 1/2007 | James et al. |
| D541,418 | S | 4/2007 | Schechter et al. |
| D541,938 | S | 5/2007 | Kerr et al |
| D564,662 | S | 3/2008 | Moses et al. |
| 7,367,973 | B2 | 5/2008 | Manzo et al. |
| D576,932 | S | 9/2008 | Strehler |
| 7,435,112 | B1 | 10/2008 | Miller et al. |
| D594,736 | S | 6/2009 | Esjunin |
| D594,737 | S | 6/2009 | Kelly et al. |
| D606,203 | S | 12/2009 | Husheer et al. |
| D613,412 | S | 4/2010 | DeCarlo |
| D634,010 | S | 3/2011 | DeCarlo |
| 2007/0055219 | A1 | 3/2007 | Whitman et al. |
| 2011/0137323 | A1 | 6/2011 | Malkowski et al. |
| 2012/0191091 | A1 | 7/2012 | Allen |

FOREIGN PATENT DOCUMENTS

| | | |
|---|---|---|
| DE | 390937 C | 3/1924 |
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4303882 A1 | 8/1994 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| EP | 0 246 350 A1 | 11/1987 |
| EP | 0 521 264 A2 | 1/1993 |
| EP | 0 556 705 A1 | 8/1993 |
| EP | 0 558 429 A1 | 9/1993 |
| EP | 0 648 515 A1 | 4/1995 |
| EP | 0 836 868 A2 | 4/1998 |
| EP | 0 882 955 A1 | 12/1998 |
| EP | 1159926 A3 | 3/2003 |
| EP | 1829495 A1 | 9/2007 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 | 3/1996 |
| JP | 08252263 A | 10/1996 |
| JP | 09000492 A | 1/1997 |
| JP | 09010223 | 1/1997 |
| JP | 11244298 A | 9/1999 |
| JP | 2000342599 A | 12/2000 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 1/1965 |
| SU | 401367 A1 | 10/1973 |
| SU | 727201 A2 | 4/1980 |
| WO | 2010/035831 A1 | 4/2010 |

OTHER PUBLICATIONS

European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.

(56) References Cited

OTHER PUBLICATIONS

European Search Report EP 04027479 dated Mar. 17, 2005.
European Search Report EP 04027705 dated Feb. 10, 2005.
European Search Report EP 04710258 dated Oct. 15, 2004.
European Search Report EP 0475234.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 0501346.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
U.S. Appl. No. 13/268,142, filed Oct. 7, 2011; Bonn.
U.S. Appl. No. 13/281,605, filed Oct. 26, 2011; Prakash et al.
U.S. Appl. No. 13/290,462, filed Nov. 7, 2011; Bonn.
U.S. Appl. No. 13/298,461, filed Nov. 17, 2011; Buysse et al.
U.S. Appl. No. 13/344,753, filed Jan. 6, 2012; Lee et al.
U.S. Appl. No. 13/343,788, filed Jan. 5, 2012; Reid, Jr.
U.S. Appl. No. 13/344,790, filed Jan. 6, 2012; Lee et al.
U.S. Appl. No. 13/351,463, filed Jan. 17, 2012; Smith et al.
U.S. Appl. No. 13/351,553, filed Jan. 17, 2012; Mahajan et al.
U.S. Appl. No. 13/358,129, filed Jan. 25, 2012; Brannan.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.
European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.

(56) References Cited

OTHER PUBLICATIONS

International Search Report PCT/US02/01890 dated Jul. 25, 2002.
International Search Report PCT/US02/11100 dated Jul. 16, 2002.
International Search Report PCT/US03/09483 dated Aug. 13, 2003.
International Search Report PCT/US03/22900 dated Dec. 2, 2003.
International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT1US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
European Search Report EP 13164267 dated Aug. 21, 2013.
Chinese Office Action issued in corresponding application No. CN 20131044408.1 on Apr. 5, 2015.
U.S. Appl. No. 12/861,333, filed Aug. 23, 2010; Brannan.
U.S. Appl. No. 12/944,951, filed Nov. 12, 2010; Brannan.
U.S. Appl. No. 12/977,390, filed Dec. 23, 2010; Brannan.
U.S. Appl. No. 12/977,415, filed Dec. 23, 2010; Brannan.
U.S. Appl. No. 12/985,124, filed Jan. 5, 2011; Brannan.
U.S. Appl. No. 12/985,136, filed Jan. 5, 2011; Brannan.
U.S. Appl. No. 12/985,155, filed Jan. 5, 2011; Brannan.
U.S. Appl. No. 12/985,179, filed Jan. 5, 2011; Brannan.
U.S. Appl. No. 13/020,562, filed Feb. 3, 2011; Brannan.
U.S. Appl. No. 13/020,664, filed Feb. 3, 2011; Bonn.
U.S. Appl. No. 13/024,041, filed Feb. 9, 2011; Brannan.
U.S. Appl. No. 13/029,521, filed Feb. 17, 2011; Brannan.
U.S. Appl. No. 13/029,594, filed Feb. 17, 2011; Brannan.
U.S. Appl. No. 13/043,665, filed Mar. 9, 2011; Willyard.
U.S. Appl. No. 13/043,694, filed Mar. 9, 2011; Willyard.
U.S. Appl. No. 13/050,729, filed Mar. 17, 2011; Ladtkow.
U.S. Appl. No. 13/083,185, filed Apr. 8, 2011; DeCarlo.
U.S. Appl. No. 13/083,256, filed Apr. 8, 2011; Brannan.
U.S. Appl. No. 13/113,736, filed May 23, 2011; Ladtkow et al.
U.S. Appl. No. 13/118,929, filed May 31, 2011; Bonn et al.
U.S. Appl. No. 13/206,075, filed Aug. 9, 2011; Lee et al.
U.S. Appl. No. 13/236,997, filed Sep. 20, 2011; Behnke II, et al.
U.S. Appl. No. 13/237,068, filed Sep. 20, 2011; Behnke II, et al.
U.S. Appl. No. 13/237,187, filed Sep. 20, 2011; Behnke II, et al.
U.S. Appl. No. 13/237,342, filed Sep. 20, 2011; Behnke II, et al.
U.S. Appl. No. 13/237,488, filed Sep. 20, 2011; Behnke II, et al.
U.S. Appl. No. 13/267,369, filed Oct. 6, 2011; Prakash et al.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product Instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" In William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard", Advanced Input Systems, <http://www.advanced-input.com/lightkey> (2002).
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.

(56) References Cited

OTHER PUBLICATIONS

Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries, Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSureTM Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radial, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.

Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences—Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 110-415, 1997.

(56) References Cited

OTHER PUBLICATIONS

T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.

LIMITED REUSE ABLATION NEEDLES AND ABLATION DEVICES FOR USE THEREWITH

CROSS-REFERENCE TO RELATED APPLICATIONS

This application is a continuation application of U.S. patent application Ser. No. 13/460,440, filed on Apr. 30, 2012, now U.S. Pat. No. 9,364,278, the entire contents of which are incorporated herein by reference.

BACKGROUND

Technical Field

The present disclosure relates to surgical instruments and, more particularly, to ablation devices including disposable needles configured for single-use or a limited amount and/or number of uses.

Background of Related Art

Energy-based tissue treatment is well known in the art. Various types of energy (e.g., electrosurgical, ultrasonic, microwave, cryogenic, thermal, laser, etc.) are applied to tissue to achieve a desired result, e.g., to cut, ablate, coagulate, and/or seal tissue.

Electrosurgery involves the application of radio frequency (RF) energy to a surgical site to cut, ablate, coagulate, and/or seal tissue. In monopolar electrosurgery, a source or active electrode, which is typically part of the surgical instrument held by the surgeon, delivers RF electrical current from a generator to tissue, while a patient return electrode is placed remotely from the active electrode to carry the current back to the generator.

In tissue ablation electrosurgery, for example, the RF energy may be delivered to targeted tissue by a probe or needle. More specifically, in use, the needle is typically advanced through tissue to a desired position either prior to or during application of energy to tissue. After repeated use, these needles may become dull, bent, or otherwise deformed and, consequently, may become more difficult to place and operate upon subsequent use. As such, ablation devices have been developed which include replaceable needles, thus allowing the needle to be replaced after one or more uses without requiring replacement of the entire device (e.g., the handpiece).

SUMMARY

As used herein, the term "distal" refers to the portion that is being described which is further from a user, while the term "proximal" refers to the portion that is being described which is closer to a user. Further, to the extent consistent with one another, any of the aspects described herein may be used in conjunction with any of the other aspects described herein.

In accordance with aspects of the present disclosure, a surgical instrument is provided generally including a reusable component and a limited-use component releasably engagable with the reusable component. The limited-use component is configured for one or more uses and includes a clocking mechanism configured to count each engagement of the reusable component and the limited-use component to one another. The clocking mechanism is incrementally transitioned upon each successive count from one or more use states (corresponding to the number of uses of the limited-use component), wherein the clocking mechanism permits both mechanical engagement and electrical coupling of the reusable component and the limited-use component to one another, to a spent state, wherein the clocking mechanism inhibits both mechanical engagement and electrical coupling of the limited-use component and the reusable component to one another.

In one aspect, the limited-use component is configured for a pre-determined plurality of uses. In such an aspect, the clocking mechanism is incrementally transitionable from a plurality of use states, each corresponding to one of the pre-determined plurality of uses, to the spent state.

In still another aspect, the clocking mechanism includes a hub and a housing. The hub is disposed within the housing and is rotatably and longitudinally movable relative to the housing to incrementally transition the clocking mechanism from the one or more use states to the spent state. Further, the housing may defines a three-dimensional track on an interior surface thereof that is configured to guide translation and rotation of the hub relative to the housing.

In yet another aspect, the reusable component includes a contact member configured for insertion into the limited-use component for mechanically engaging the reusable component and the limited-use component to one another and for triggering a count of the clocking mechanism.

In still yet another aspect, the clocking mechanism further includes indicia configured to display a condition of the limited-use component. More specifically, the indicia may be configured to displays a number of uses remaining for the limited-use component.

In another aspect, the clocking mechanism is further transitionable to a locked state to inhibit manual overriding of the clocking mechanism.

In yet another aspect, the surgical instrument includes an ablation device having a reusable handle assembly and a limited-use electrode assembly that is releasably engagable with the reusable handle assembly.

In still another aspect, the reusable component is configured to supply fluid to the limited-use component. In such an aspect, the supply of fluid to the limited-use component may trigger a count of the clocking mechanism.

An ablation device provided in accordance with aspects of the present disclosure generally includes a reusable handle assembly configured to connect to a source of energy and including a contact member. A limited-use electrode assembly is configured receive the contact member of the reusable handle assembly for mechanically engaging and electrically coupling the reusable handle assembly and the limited-use electrode assembly for transmitting energy to tissue to treat tissue. The limited-use electrode assembly is configured for one or more uses and includes a clocking mechanism. The clocking mechanism is configured to count each use of the limited-use electrode assembly and to incrementally transition upon each successive count from the one or more use states, wherein engagement of the reusable handle assembly and the limited-use electrode assembly is permitted, to a spent state, wherein the clocking mechanism inhibits engagement of the limited-use electrode assembly and the reusable handle assembly to one another. Insertion of the contact member of the reusable handle assembly into the limited-use electrode assembly triggers a count of the clocking mechanism.

In one aspect, the clocking mechanism further includes indicia configured to display a condition of the limited-use electrode assembly. More specifically, the indicia may be configured to display a number of uses remaining for the limited-use electrode assembly.

In another aspect, the limited-use electrode assembly is configured for a pre-determined plurality of uses. In such an aspect, the clocking mechanism is incrementally transitionable from a plurality of use states, each corresponding to one of the pre-determined plurality of uses, to the spent state.

In still another aspect, the clocking mechanism is further transitionable to a locked state to inhibit manual overriding of the clocking mechanism.

Provided in accordance with aspects of the present disclosure is a surgical instrument generally including a reusable component configured to connect to a source of fluid and a limited-use component releasably engagable with the reusable component. The limited-use component is configured to receive fluid from the reusable component and includes a clocking mechanism. The clocking mechanism is configured to count each successive use of the limited-use component upon supply of fluid to the limited-use component and to incrementally transition upon each successive count from one or more use states, wherein the clocking mechanism permits both mechanical engagement and electrical coupling of the reusable component and the limited-use component to one another, to a spent state, wherein the clocking mechanism inhibits both mechanical engagement and electrical coupling of the limited-use component and the reusable component to one another.

In one aspect, the limited-use component is configured for a pre-determined plurality of uses. Accordingly, the clocking mechanism is incrementally transitionable from a plurality of use states, each corresponding to one of the pre-determined plurality of uses, to the spent state.

In still another aspect, the clocking mechanism further includes indicia configured to display a condition of the limited-use component. More specifically, the indicia may be configured to display a number of uses remaining for the limited-use component.

In yet another aspect, the surgical instrument includes an ablation device having a reusable handle assembly and a limited-use electrode assembly releasably engagable with the reusable handle assembly.

BRIEF DESCRIPTION OF THE DRAWINGS

Various aspects of the present disclosure are described herein with reference to the drawings wherein like reference numerals identify similar or identical elements.

DETAILED DESCRIPTION

Figure 1:
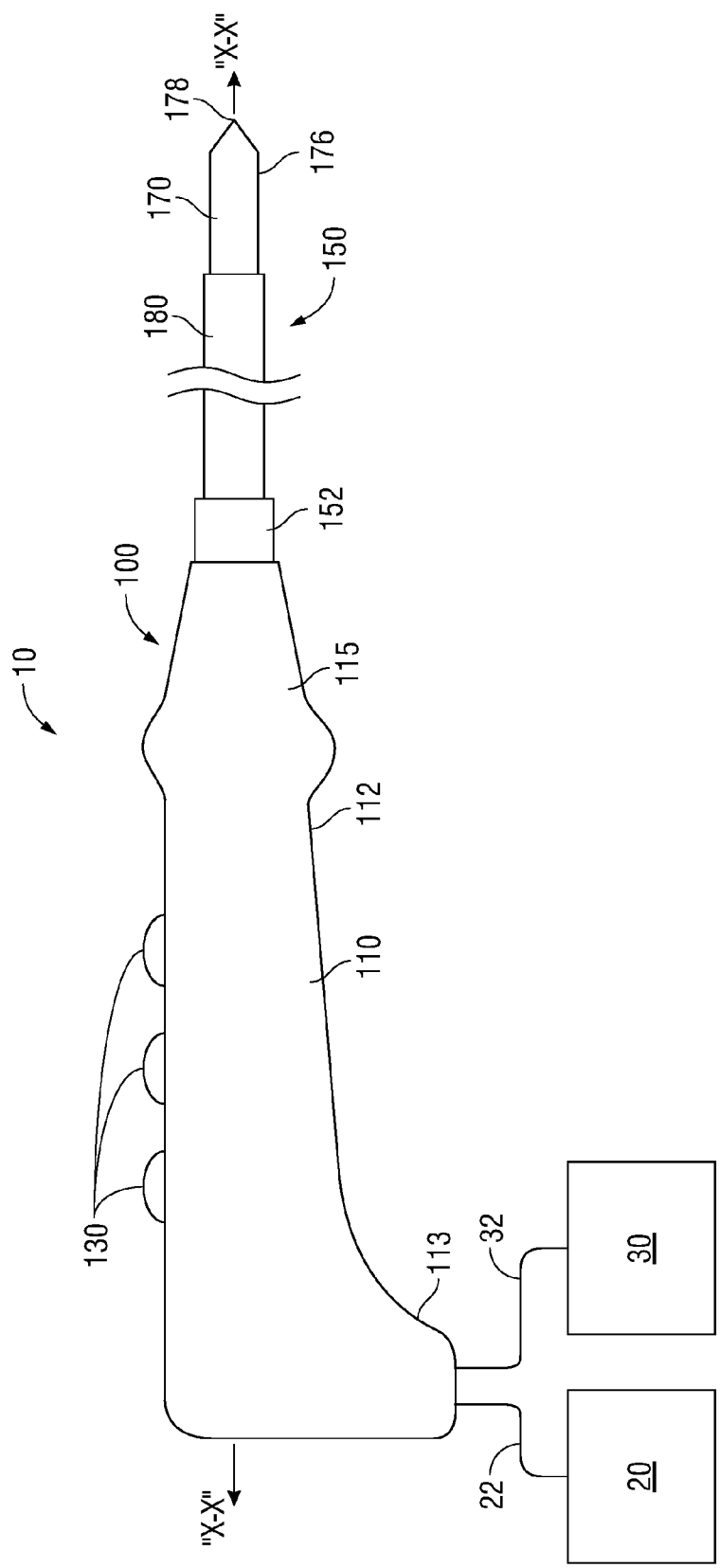
FIG. 1 is a side view of an electrosurgical ablation system provided in accordance with the present disclosure.
Figure 2:
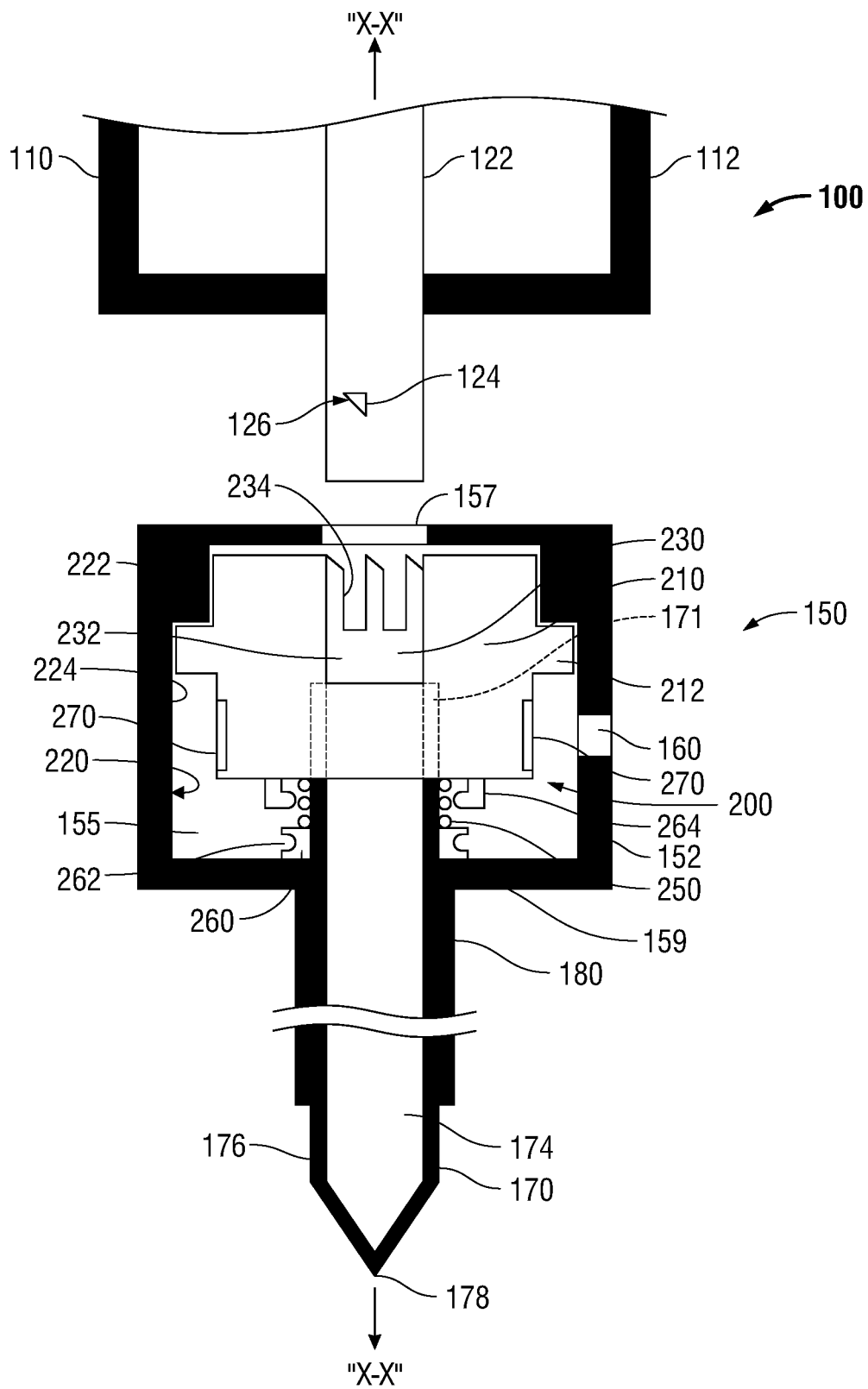
FIG. 2 is a longitudinal, cross-sectional view of a distal end of the electrosurgical ablation system of FIG. 1 with a needle electrode assembly disengaged from a handle assembly thereof.

Referring initially to FIGS. 1-2, an ablation system provided in accordance with the present disclosure is shown generally designated by reference numeral 10. Although ablation system 10 is shown configured as an RF-ablation system 10, the present disclosure is equally applicable for use with microwave ablation systems, or any other suitable surgical system including single-use or limited-use disposable components. Obviously, different considerations apply depending on the particular device and/or system used; however, the novel aspects with respect to inhibiting or limiting re-use of the needle (or other component) remains generally consistent regardless of the particular type of device and/or system used. For the purposes herein, ablation system 10 is generally described.

Continuing with reference to FIGS. 1-2, ablation device 100 of ablation system 10 generally includes a handle assembly 110 and a needle electrode assembly 150 releasably engagable with and extending from handle assembly 110. Although only one needle electrode assembly 150 is shown, additional needle electrode assemblies, either similar to or different from needle electrode assembly 150, may be provided for releasable engagement with handle assembly 110. As such, a desired needle electrode assembly may be selected and engaged to handle assembly 110, depending on a particular purpose and/or to replace a "spent" needle.

Handle assembly 110 includes a housing 112 which may be ergonomically or otherwise configured to facilitate the grasping and manipulation of housing 112 by a user to position needle electrode assembly 150 as desired. Housing 112 is formed from an insulative material and defines proximal and distal ends 113, 115, respectively. Proximal end 113 of housing is configured to receive lines 22, 32 from an energy source, e.g., generator 20, and cooling fluid source 30, respectively, for supplying energy and cooling fluid, respectively, to needle electrode assembly 150. Contact pin 122 extends from distal end 115 of housing 112 and is configured for insertion into housing 152 of needle electrode assembly 150 for engaging needle electrode assembly 150 and handle assembly 110 to one another. More specifically, contact pin 122 is insertable through housing 152 and into engagement within proximal end 171 of needle 170, e.g., in friction-fit engagement therewith to releasably mechanically engage needle electrode assembly 150 and handle assembly 110 to one another. Other releasable engagement mechanisms, e.g., snap-fit engagements, are also contemplated.

With continued reference to FIGS. 1-2, handle assembly 110, as mentioned above, includes an electrical contact pin 122 (although greater or fewer contacts are also contemplated) extending distally therefrom that is configured for insertion into proximal end 171 of needle 170 of needle electrode assembly 150 to establish electrical communication between handle assembly 110 and needle electrode assembly 150 upon mechanical engagement of handle assembly 110 and needle electrode assembly 150. One or more wires (not explicitly shown) extending through housing 112 of handle assembly 110 couple contact pin 122 to line 22, which extends proximally from housing 112 of handle assembly 110, ultimately coupling to generator 20.

Figure 6A:
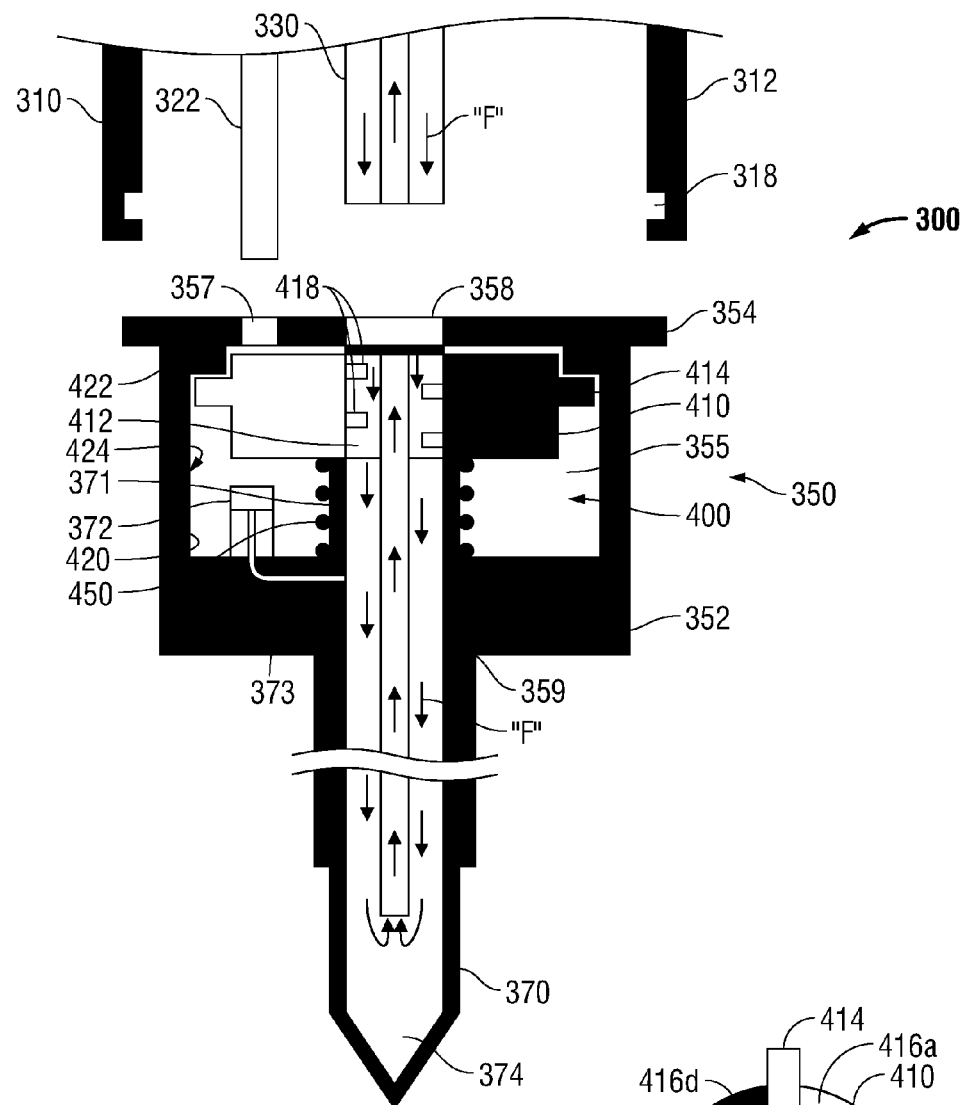
FIG. 6A is a longitudinal, cross-sectional view of a distal end of another electrosurgical ablation device provided in accordance with the present disclosure, showing a needle electrode assembly and handle assembly during engagement to one another.
Figure 6B:
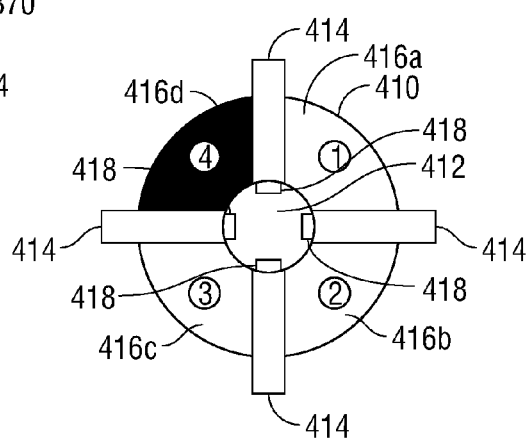
FIG. 6B is a transverse, cross-sectional view of a clocking mechanism of the electrosurgical ablation system of FIG. 6A.

As such, power and/or control signals may be transmitted between generator 20 and needle electrode assembly 150. In particular, contact pin 122 may be configured for establishing a conductive path for transmission of energy between generator 20 and needle 170 of needle electrode assembly 150. As such, upon activation, energy can be transmitted from generator 20 to needle electrode assembly 150 and, ultimately, conducted through tissue to ablate or otherwise treat tissue. One or more lumens (not explicitly shown) extending through contact pin 122 may also be provided for circulation of cooling fluid from a cooling fluid source 30 through hollow interior 174 of needle 170, similarly as described below with respect to ablation device 300 (FIGS. 6A-6B). As an alternative to external generator 20, it is contemplated that generator 20 be incorporated into handle assembly 110, thus providing a hand-held ablation device 100.

Contact pin 122 (or other electrical contacts (not shown)) may additionally or alternatively be utilized for identifying or verifying the identification of the particular type of needle electrode assembly 150 engaged with handle assembly 110. This feature helps ensure that an acceptable needle electrode assembly 150 has been engaged to handle assembly 110 and/or that the proper energy delivery and control parameters for the particular needle electrode assembly 150 engaged with handle assembly 110 are provided by generator 20. Further, the operation of cooling fluid source 30 may also be at least partially dependent upon the particular type of needle electrode assembly 150 detected. Thus, identifying information for the particular type of needle electrode assembly 150 engaged to handle assembly 110 may be relayed to and utilized by cooling fluid source 30 for controlling the supply of cooling fluid to the needle electrode assembly 150 in accordance therewith. Other configurations of contact(s) or similar features for establishing electrical communication and electrical energy transmission between handle assembly 110 and needle electrode assembly 150 are also contemplated.

Needle electrode assembly 150 defines a longitudinal axis "X-X" and includes a housing 152 disposed at the proximal end thereof and an electrically-conductive needle 170 disposed partially within housing 152 and extending distally from housing 152. Housing 152 is formed from an electrically-insulative material and includes an internal cavity 155 configured to receive contact pin 122 of handle assembly 110 and needle 170 for engagement of contact pin 122 and needle 170 to one another. Internal cavity 155 of housing 152 incorporates a clocking mechanism 200 therein that is configured to count the number of uses of needle electrode assembly 150, e.g., the number of times needle electrode assembly 150 has been engaged to handle assembly 110, and to inhibit subsequent use of needle electrode assembly 150 once the pre-determined number of uses of needle electrode assembly 150 has been achieved. Clocking mechanism 200 will be described in greater detail below.

Needle 170 of needle electrode assembly 150 defines a hollow interior 174 and includes an insulative sleeve (or coating) 180 disposed about a portion of the external surface of needle 170. Proximal end 171 of needle 170, as mentioned above, is configured to mechanically engage and electrical couple to contact pin 122 of handle assembly 110, e.g., proximal end 171 of needle 170 is configured to extend into housing 152 of needle electrode assembly 150 to receive contact pin 122 of handle assembly 110 therein in friction-fit engagement therewith (although other suitable engagements are also contemplated), to mechanically engage and electrically couple needle electrode assembly 150 and handle assembly 110 to one another. Needle 170 extends distally from housing 152 to distal end 176 thereof, which defines a distal tip 178 configured to facilitate the penetration of tissue while minimizing the risk of hemorrhage from the puncture tract, although other distal tip configurations are also contemplated. Needle 170 is formed from an electrically-conductive material of which at least distal end 176 is exposed. Insulative sleeve 180 is disposed about a portion of needle 170 such that at least distal end 176 of needle 170 exposed. With distal end 176 of needle 170 exposed, energy, e.g., RF energy, can be delivered from needle 170 to surrounding tissue to treat, e.g., ablate, tissue.

As mentioned above, an energy source, e.g., generator 20, is provided for providing power and/or control signals to needle electrode assembly 150 via line 22 and contact pin 122. Further, cooling fluid source 30 and line 32 are provided for providing cooling fluid to needle electrode assembly 150, e.g., via one or more lumens (not explicitly shown) extending through contact pin 122 and into communication with hollow interior 174 of needle 170 (similarly as described below with respect to ablation device 300 (FIGS. 6A-6B). That is, cooling fluid source 30 provides cooling fluid, via line 32 (which includes both inflow and outflow lines), such that cooling fluid supplied by the cooling fluid source 30 may be circulated through hollow interior 174 of needle 170 to maintain needle electrode assembly 150 in a relatively cooled state during the application of energy to tissue. Cooperating valves (not shown) of needle electrode assembly 150 and handle assembly 110 may be provided to facilitate and/or regulate the passage, e.g., inflow and outflow, of the cooling fluid between cooling fluid source 30 and hollow interior 174 of needle 170, although other configurations are also contemplated. Circulation of the cooling fluid may be established through the use of a pump (not shown) or other suitable mechanism disposed within housing 112 of handle assembly 110, or the pump (not shown) may be externally disposed.

In operation, ablation device 100, led by distal tip 178 of needle 170, is inserted into an operative site such that exposed distal end 176 of needle 170 of ablation device 100 is positioned adjacent to or within a target tissue to be treated, e.g., ablated. A return pad or return electrode (not shown) may, at this point or prior to, be operatively-adhered to or connected to the patient. With exposed distal end 176 of needle 170 in position, energy, e.g., RF energy, is delivered from generator 20 to needle 170 and is conducted from exposed distal end 176 of needle 170 through the target tissue, ultimately to be collected by the return electrode (not shown). An effective amount of energy at an effective energy level and for an effective duration of time is delivered to tissue to achieve the desired result, e.g., to treat the target tissue. To this end, one or more control switches 130 may be provided on handle assembly 110 for controlling the supply of energy to needle 170, or, alternatively, the supply of energy may be automatically or manually controlled by generator 20.

Either prior to or simultaneously with the delivery of electrosurgical energy to needle 170, the cooling fluid provided by cooling fluid source 30 may be circulated through hollow interior 174 of needle 170 to withdraw heat from needle 170, thus maintaining needle 170 in a relatively cooled state during use. The delivery of cooling fluid to hollow interior 174 of needle 170 may likewise be controlled by one or more control switches 130 disposed on handle assembly 110, or via cooling fluid supply 30 itself.

At the completion of the procedure, needle electrode assembly 150 may be disengaged from handle assembly 110 and both may be sterilized for reuse. Ultimately, needle electrode assembly 150 may be re-engaged to handle assembly 110 (or may be engaged to another handle assembly) for subsequent use. However, although needle electrode assembly 150 is configured for repeated use, the number of uses of needle electrode assembly 150 is limited via clocking mechanism 200, thus inhibiting needle electrode assembly 150 from being used, e.g., re-engaged to handle assembly 110 or another handle assembly, beyond the pre-determined number of uses set via clocking mechanism 200. The features and operation of clocking mechanism 200 are described in detail below.

With reference to FIGS. 2-5B, clocking mechanism 200 of ablation device 100 generally includes a hub 210 operably disposed within housing 152 of needle electrode assembly 150. Housing 152 defines an internal cavity 155 and includes a proximal opening 157 in communication with cavity 155 that is configured to receive contact pin 122 of handle assembly 110 therethrough and a distal opening 159 in communication with cavity 155 that is configured to receive needle 170 therethrough. The internal surface 220 of housing 152 that defines cavity 155 defines a shoulder 222 and a three-dimensional track 224 that, as will be described in greater detail below, are configured to guide translation and rotation of hub 210 relative to housing 152. A spring 250 disposed about needle 170 and positioned within cavity 155 between the distal end of housing 152 and hub 210 is configured to bias hub 210 proximally. Further, first and second lock apertures 262 defined within respective lock members 260 are configured to engage corresponding lock fingers 264 extending distally from hub 210 to lock hub 210 and, thus, needle electrode assembly 150 in the "spent" condition, as will be described below. Housing 152 also includes a transverse window 160 configured to permit visualization of hub 210 from the exterior of housing 152 such that the user may determine the condition of needle electrode assembly 150, e.g., the number of uses needle electrode assembly 150 has remaining.

Hub 210 of clocking mechanism 200 includes a plurality of angled flanges 212 (see FIG. 5A) extending outwardly therefrom. Flanges 212 are initially disposed in abutting relation with shoulder 222 of housing 152 under the bias of spring 250, and are configured to translate along three-dimensional track 224 of internal surface 220 of housing 152 to "clock" or count the number of uses of needle electrode assembly 150. Hub 210 further defines a central lumen 230 extending therethrough. More specifically, needle 170 extends at least partially into central lumen 230 of hub 210 and is engaged therein such that hub 210 is disposed at least partially about needle 170. Due to this configuration, wherein hub 210 and needle 170 are engaged to one another, both hub 210 and needle 170 are rotationally and longitudinally movable relative to housing 152.

With continued reference to FIGS. 2-5B, the internal surface 232 of hub 210 that defines central lumen 230 defines a track 234 configured to receive angled protrusions 124 (although only one is shown and described for simplicity purposes) disposed about contact pin 122 of handle assembly 110 upon insertion of contact pin 122 through proximal opening 157 of housing 152, central lumen 230 of hub 210, and into engagement with needle 170 for mechanically engaging and electrically coupling handle assembly 110 and needle electrode assembly 150 to one another. As will be described in greater detail below, angled protrusion 124 facilitates the rotation of hub 210 upon insertion of contact pin 122 into engagement with needle 170 to "count" each successive use, e.g., each successive engagement of needle electrode assembly 150 to handle assembly 110, of needle electrode assembly 150.

Hub 210 of clocking mechanism 200 further includes visual markings or indicia 270, e.g., numbers, symbols, color-coding, etc., disposed about the outer peripheral surface thereof. Indicia 270 are positioned such that the indicium 270 corresponding to the number of uses remaining for (or the condition of) needle electrode assembly 150 is visible through window 160 of housing 152. More specifically, after each use, the incremental rotation of hub 210 relative to housing 152 repositions the next indicium 270 adjacent window 160, thereby presenting to the user the condition/status of needle electrode assembly 150. The various indicia 270 may include numbers corresponding to the number of uses left. Alternatively or additionally, the various indicia 270 may be color coded, e.g., to include green indicia indicating that the needle electrode assembly 150 has several uses left, red indicia indicating that the needle electrode assembly 150 is "spent," or no longer usable, and yellow indicia indicating that only single use (or few uses) is remaining. Other configurations are also contemplated, for example, the use of a digital indicator (not explicitly shown).

Figure 4:
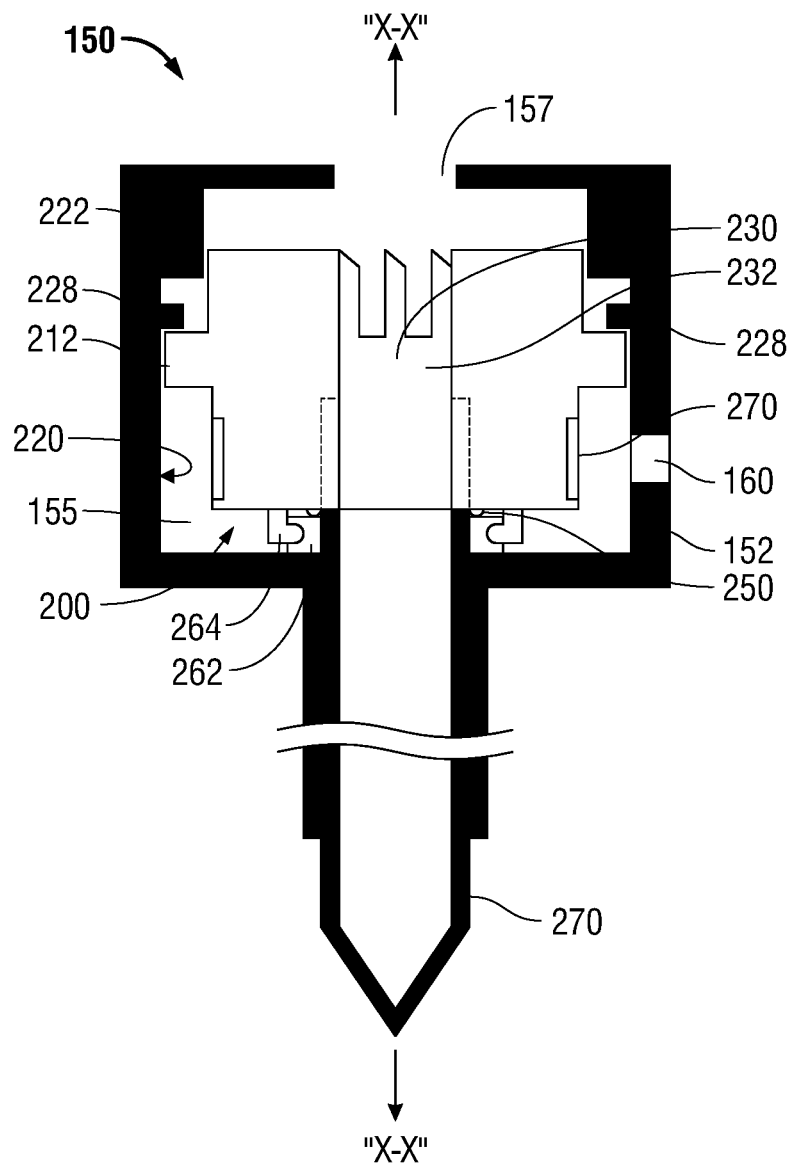
FIG. 4 is a longitudinal, cross-sectional view of the needle electrode assembly of the electrosurgical ablation system of FIG. 1, wherein a clocking mechanism of the needle electrode assembly is disposed in a locked-out condition.
Figure 5A:
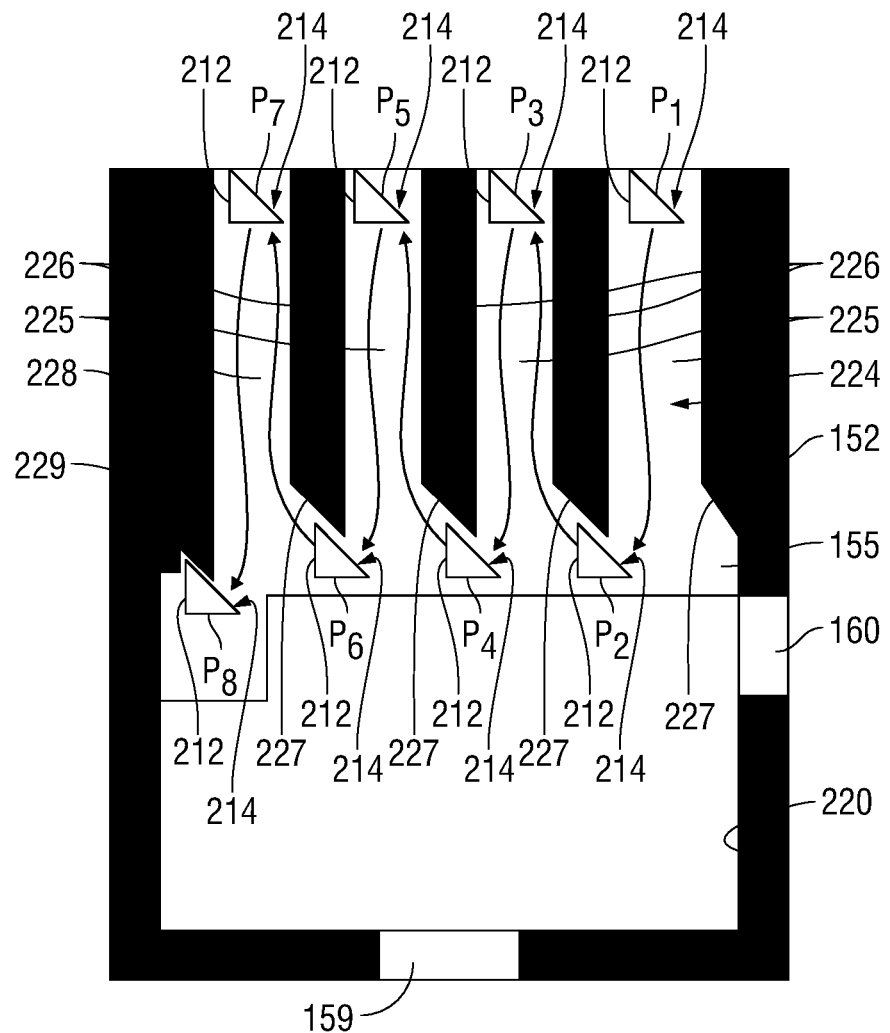
FIG. 5A is a schematic illustration of an interior surface of a housing of the needle electrode assembly of the electrosurgical ablation system of FIG. 1, illustrating a hub of the clocking mechanism moving relative thereto.

As best shown in FIG. 5A, the three-dimensional track 224 of housing 152 is defined annularly about interior surface 220 of housing 152 and includes one or more sets of alternating channels 225 and bars 226 extending from the proximal end of housing 152 towards the distal end thereof. Bars 226 each define an angled distal surface 227. A final bar 228 defining a ceiling 229 is disposed adjacent each set of channels 225 and bars 226 for retaining clocking mechanism 200 in the locked position when the needle electrode assembly 150 (FIGS. 2-4) has reached its usage limit. With additional reference to FIGS. 2-4, flanges 212 of hub 210 define right-triangle-shaped configurations (although other configurations are contemplated), each having an angled surface 214 sloped complementarily to angled distal surfaces 227 of bars 226. Each flange 212 corresponds to one set of alternating channels 225 and bars 226, although only one flange 212 and the corresponding set of channels 225 and bars 226 thereof is described (and shown in FIG. 5A) for purposes of simplicity. Flange 212 is movable through the channels 225 and about the bars 226 thereof before ultimately being engaged within final bar 228 to inhibit further use. That is, as will be described in greater detail below, flange 212 moves proximally and distally through channels 225 and about bars 226 to "count" the uses of needle electrode assembly 150 before being engaged within final bar 228, to inhibit further use.

Figure 5B:
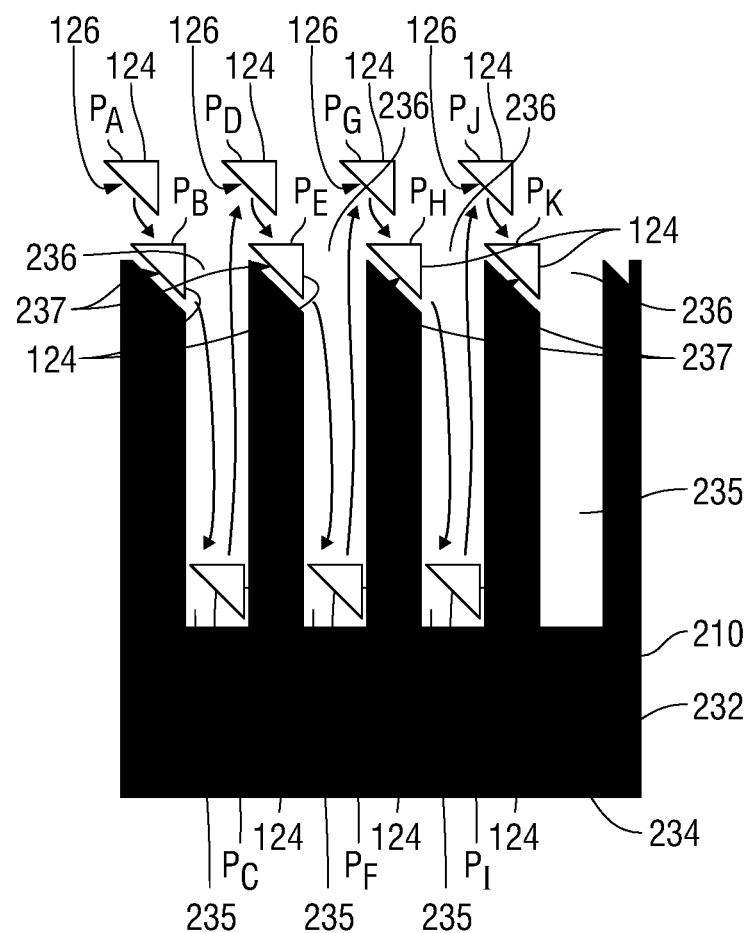
FIG. 5B is a schematic illustration of an interior surface of the hub of the needle electrode assembly of the electrosurgical ablation system of FIG. 1, illustrating a contact pin of the handle assembly moving relative thereto.

As best shown in FIG. 5B, track 234 defined within internal surface 232 of central lumen 230 of hub 210 includes a plurality of slots 235, each including a mouth 236 defining the open end of the slot 235. Mouths 236 each define an angled surface 237 configured to mate with a complementarily-sloped angled surface 126 of angled protrusion 124 disposed on the outer periphery of contact pin 122 (see FIGS. 2-4). With additional reference to FIGS. 2-4, in use, as will be described in greater detail below, angled surface 126 of angled protrusion 124 mate with angled surfaces 237 of mouths 236 upon insertion of contact pin 122 into central lumen 230 of hub 210 to urge hub 210 distally. Eventually, after hub 210 has been translated sufficiently distally, angled surfaces 126, 237 slide past one another such that hub 210 is rotated about contact pin 122 and relative to housing 152. Rotation of hub 210 allows angled protrusion 126 to move into the adjacent slot 235, thus permitting hub 210 to return proximally under the bias of spring 250 to facilitate engagement of contact pin 122 and needle 170 while also "counting" the use of needle electrode assembly 150.

Figure 3:
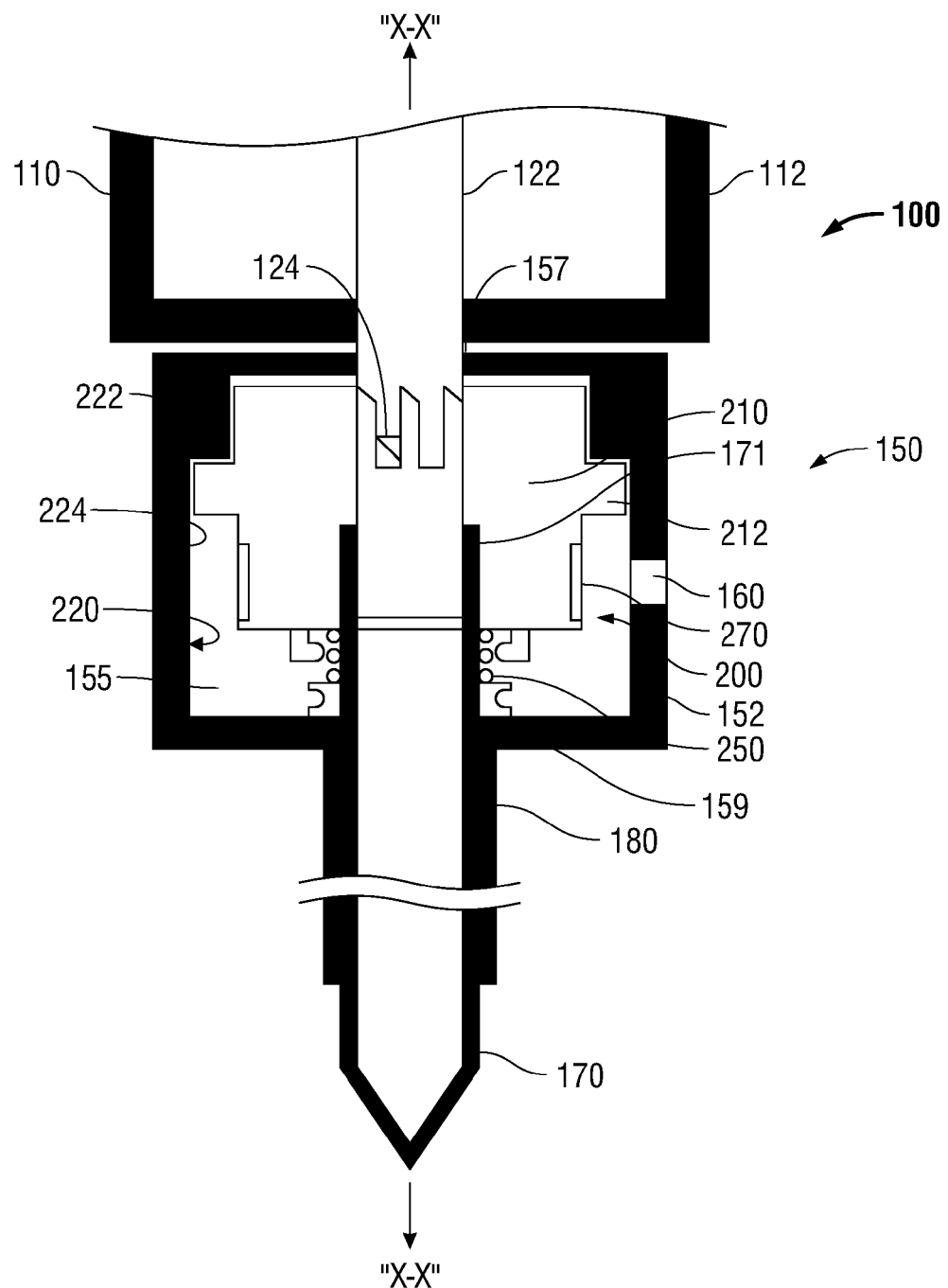
FIG. 3 is a longitudinal, cross-sectional view of the electrosurgical ablation system of FIG. 1 with the needle electrode assembly engaged to the handle assembly.

With reference to FIGS. 2-4, in conjunction with FIGS. 5A-5B, the assembly of ablation device 100 and operation of clocking mechanism 200 thereof is described, wherein particular features and functions of clocking mechanism 200 will become more apparent. Initially, as shown in FIG. 2, needle electrode assembly 150 is disposed in an unused position condition wherein hub 210 is disposed in a first, or unused rotational position and is biased proximally by spring 250 such that flange 212 abut shoulder 222 of housing 152. At this point, as shown in FIG. 5A, flange 212 is disposed at position $P_1$ relative to the respective set of channels 225 and bars 226 thereof and the indicium 270 aligned with window 160 of housing 152 corresponds to the number of uses of needle electrode assembly 150 remaining, e.g., three (3) uses. Further, in this position, lock fingers 264 are spaced-apart from lock apertures 262.

With particular reference to FIGS. 2-3, in conjunction with FIGS. 5A-5B, in order to engage needle electrode assembly 150 to handle assembly 100 needle electrode assembly 150 and handle assembly 100 are approximated relative to one another such that contact pin 122 is inserted into central lumen 230 of hub 210. As contact pin 122 is inserted into central lumen 230 of hub 210, angled protrusion 124 of contact pin 122 is moved from position $P_A$ to position $P_B$ such that angled surfaces 126, 237 mate with one another. With angled surfaces 126, 237 mating with one another, further insertion of contact pin 122 urges angled surface 126 of protrusion 124 of contact pin 122 further into angled surface 237 of hub 210, thereby translating hub 210 and needle 170 distally relative to housing 152 and against the bias of spring 250. Angled protrusion 124 of contact pin 122 is retained in rotational position relative to angled surface 237 of mouth 236 of hub 210 at this point, e.g., in position $P_B$, since the disposition of flange 212 within channel 225 inhibits rotation of hub 210 as hub 210 is translated distally relative to housing 152.

Continuing with reference to FIGS. 2-3, in conjunction with FIGS. 5A-5B, upon further insertion of contact pin 122 into housing 152 of needle electrode assembly 150, angled protrusion 124 of contact pin 122 urges hub 210 further distally such that flange 212 of hub 210 clears the distal end of the adjacent bar 226, e.g., such that flange 212 is disposed in position $P_2$. More specifically, once flange 212 of hub 210 is moved distally beyond the adjacent bar 226, hub 210 is no longer inhibited from rotating and, as such, the bias of spring 250 urges hub 210 proximally such that angled surfaces 214, 227 slide past one another and such that angled surfaces 126, 237 slide past one another to rotate hub 210 relative to housing 152 and contact pin 122 from the first rotational position to a second rotational position. Rotation of hub 210 relative to housing 152 and contact pin 122 moves flange 212 into the next channel 225 and moves protrusion 124 of contact pin 122 into the adjacent slot 235. With flange 212 disposed at the distal end of the next channel 225 and with protrusion 124 disposed at the proximal end of the adjacent slot 235, hub 210 is no longer inhibited from proximal movement and, thus is returned proximally under the bias of spring 250 and relative to housing 152 and contact pin 122. Accordingly, flange 212 is moved relatively proximally through the channel 225 to position $P_3$ and protrusion 124 is moved relatively distally through the slot 235 to position $P_C$. As hub 210 is translated proximally, needle 170 is likewise moved proximally until needle 170 is brought into contact, e.g., surrounding friction-fit contact (or other suitable engagement, e.g., snap-fit), with contact pin 122, thereby mechanically engaging handle assembly 110 and needle electrode assembly 150 and establishing electrical communication therebetween. That is, handle assembly 110 and needle electrode assembly 150 are simultaneously or near-simultaneously mechanically engaged and electrically coupled to one another, while hub 210 is rotated to the second rotational position such that the corresponding indicium 270 is visible through window 160 of housing 152 to indicate the number of uses needle electrode assembly 150 has remaining, e.g., to indicate two (2) remaining uses.

With handle assembly 110 and needle electrode assembly 150 mechanically engaged and electrically coupled to one another, as shown in FIG. 3, ablation device 100 may be used similarly as describe above to treat, e.g., ablate, tissue. After use, needle electrode assembly 150 may be disengaged from handle assembly 110 via moving handle assembly 110 and needle electrode assembly 150 apart from one another with sufficient urging (or to otherwise disengage the mechanical engagement therebetween) to remove contact pin 122 from central lumen 230 of hub 210. At this point, hub 210 remains disposed in the second rotational position, wherein flange 212 is disposed at position $P_3$.

Referring still to FIGS. 2-3, in conjunction with FIGS. 5A-5B, after sterilization, needle electrode assembly 150 may be re-engaged to handle assembly 110 for re-use. The engagement of needle electrode assembly 150 and handle assembly 110 is similar to that described above, except that flange 212 is moved from position $P_3$, to position $P_4$ and ultimately to position $P_5$; protrusion 124 is moved from position $P_D$ to position $P_E$ and ultimately to position $P_F$; and hub 210 is rotated from the second rotational position to a third rotational position, wherein the corresponding indicium 270 is visible through window 160, e.g., to indicate that needle electrode assembly 150 has one (1) use remaining.

In the next cycle of use, e.g., upon subsequent engagement of needle electrode assembly 150 and handle assembly 110 to one another, flange 212 is moved from position $P_5$, to position $P_6$ and ultimately to position $P_7$; protrusion 124 is moved from position $P_G$ to position $P_H$ and ultimately to position $P_I$; and hub 210 is rotated from the third rotational position to a fourth rotational position, wherein the corresponding indicium 270 is visible through window 160, e.g., to indicate that needle electrode assembly 150 is "spent."

Turning now to FIGS. 2-4, in conjunction with FIGS. 5A-5B, since needle electrode assembly 150, at this point, has reached its usage limit, needle electrode assembly 150 is to be disposed of in favor of a new needle electrode assembly 150. However, if needle electrode assembly 150 is attempted to be re-engaged to handle assembly 110, both mechanical engagement and electrical coupling are inhibited, thereby inhibiting further use of needle electrode assembly 150. More specifically, with flange 212 disposed in position $P_7$, upon insertion of contact pin 122 into central lumen 230 of hub 210, protrusion 124 is moved from position $P_J$ to position $P_K$ to urge hub 210 distally. As hub 210 is urged distally, flange 212 is translated through the channel 225 until flange 212 is disposed distally of final bar 228. With flange 212 disposed distally of final bar 228, hub 210 is permitted to rotate to a fifth, or locked rotational position, wherein flange 212 is moved to position $P_8$ to lock hub 210 in a distal position. More specifically, in this locked position, as shown in FIG. 5A, ceiling 229 of final bar 228 inhibits flange 212 and, thus, hub 210 from returning proximally, thereby inhibiting needle 170 from mechanically engaging and electrically coupling to contact pin 122. Further, in this locked position, as shown in FIG. 4, lock fingers 264 are moved into engagement within lock apertures 262 to inhibit manual overriding of this locked position, e.g., to lock hub 210 in the locked position. Accordingly, needle electrode assembly 150 is inhibited from further use.

Turing now to FIGS. 6A-6B, another embodiment of an ablation device provided in accordance with the present disclosure is shown generally identified by reference numeral 300. Ablation device 300 is similar to ablation device 100 (FIGS. 1-5B), described above, and, thus, only the differences between ablation device 300 and ablation device 100 (FIGS. 1-5B) will be described in detail below, while similarities will only be summarily described or omitted entirely. Further, to the extent consistent, any of the features of ablation device 100 (FIGS. 1-5B) may similarly be used in conjunction with ablation device 300, and vice versa.

Continuing with reference to FIGS. 6A-6B, and to FIG. 6A in particular, ablation device 300 differs from ablation device 100 (FIGS. 1-5A) mainly in that that clocking mechanism 400 of ablation device 300 includes a hub 410 disposed within housing 352 of needle electrode assembly 350 that is transitioned from the first rotational position, to the second rotational position, to the third rotational position, etc., e.g., each use of needle electrode assembly 350 is "counted," upon circulation of cooling fluid through hollow interior 374 of needle 370 of needle electrode assembly 350. The particular features, use, and operation of ablation device 300 are described in greater detail below.

With continued reference to FIG. 6A in particular, ablation device 300 generally includes a handle assembly 310 and a needle electrode assembly 350 that is releasably engagable with handle assembly 310, e.g., via the engagement of protrusions 354 of housing 352 of needle electrode assembly 350 within notches 318 defined within housing 312 of handle assembly 310. Housing 312 of handle assembly 310 is configured to couple to an energy source, e.g., generator 20 (FIG. 1), and a cooling fluid source, e.g., cooling fluid source 30 (FIG. 1) for supplying energy and cooling fluid, respectively, to needle electrode assembly 350. More specifically, an electrical contact pin 322 of handle assembly 310, which ultimately couples to generator 20 (FIG. 1), is configured to extend through a contact pin opening 357 in housing 352 of needle electrode assembly 350 to electrically couple to corresponding electrical contact 372 of needle 370 to supply energy and/or control signals to needle 370, while fluid supply lumen 330 of handle assembly 310, which ultimately couples to cooling fluid source 30 (FIG. 1), is configured for engagement within central opening 358 of housing 352 of needle electrode assembly 350 to permit the circulation of cooling fluid through central lumen 412 of hub 410 and hollow interior 374 of needle 370, as indicated by arrows "F," to maintain needle 370 in a cooled state during use.

Referring to FIGS. 6A-6B, housing 352 of needle electrode assembly 350 defines an internal cavity 355 and includes a contact pin opening 357 configured to receive contact pin 322 of handle assembly 310. An electrical contact 372 disposed within housing 352 and coupled to needle 370 via wire 373 is positioned to couple to electrical contact pin 322 upon insertion into housing 352 to electrically couple handle assembly 310 and needle electrode assembly 350 to one another. Housing 352 also includes a central opening 358 in communication with cavity 355 that is configured to receive fluid supply lumen 330 of handle assembly 310, and a distal opening 359 through which proximal end 371 of needle 370 extends. The internal surface 420 of housing 352 that defines cavity 355 defines a shoulder 422 and a three-dimensional track 244, similar to shoulder 222 and track 224 of needle electrode assembly 150 (FIGS. 2-5A), that are configured to guide translation and rotation of hub 410 relative to housing 352. A spring 450 disposed about needle 370 and positioned within cavity 355 between the distal end of housing 352 and hub 410 is configured to bias hub 410 proximally.

Hub 410 of clocking mechanism 400 is disposed within housing 352 and defines a central lumen 412 extending therethrough that is configured to establish communication between fluid supply lumen 330 and hollow interior 374 of needle 370 for inflow/outflow of cooling fluid therebetween. Hub 410 is rotationally and longitudinally movable relative to housing 352 and includes a plurality of angled flanges 414 extending outwardly therefrom that are configured to translate though track 424 of housing 352, similarly as described above with respect to ablation device 100 (see FIGS. 2-5B). Hub 410 further includes a plurality of compartments 416a, 416b, 416c, 416d (although greater or fewer than four compartments may be provided) annularly disposed about central lumen 412. One or more of the compartments, e.g., compartments 416a, 416b, 416c (corresponding to the number of pre-determined uses of needle electrode assembly 350) are hollow and, thus, are configured to permit insertion of contact pin 322 therethrough to permit electrical coupling and mechanical engagement of handle assembly 310 and needle electrode assembly 350 to one another, while final, filled compartment 416d, when moved into position adjacent contact pin opening 357 of housing 352, inhibits insertion of contact pin 322 therethrough, thus inhibiting electrical coupling and mechanical engagement of handle assembly 310 and needle electrode assembly 350 to one another.

Continuing with reference to FIGS. 6A-6B, hub 410 further includes a plurality of angled fins 418 extending inwardly therefrom into central lumen 412. Angled fins 418 are configured such that, upon distal flow of cooling fluid from fluid supply lumen 330 through central lumen 412 of hub 410 and into hollow interior 374 of needle 370, the pressure exerted by the cooling fluid on angled fins 418 urges hub 410 distally against the bias of spring 450 and, as a result of the angled configuration of fins 418, exerts a rotational force on hub 410. That is, rather than protrusions 124 of contact pin 122 urging hub 210 distally and providing rotational force thereto as in ablation device 100 (see FIGS. 2-5B), the cooling fluid flowing through central lumen 412 of hub 410 urges hub 410 distally and rotationally loads hub 410. Upon disengagement of needle electrode assembly 350 from handle assembly 310 after each use, the rotationally loaded hub 410 is rotated to the next rotational position. As such, after each use, e.g., each time needle electrode assembly 350 is engaged to handle assembly 310, cooling fluid is supplied to needle 370, and needle electrode assembly 350 is disengaged from handle assembly 310, a use of needle electrode assembly 350 is "counted" by clocking mechanism 400.

For example, as shown in FIG. 6B, needle electrode assembly 350 may be configured for three uses (although needle electrode assembly 350 may alternatively be configured for greater or fewer uses). In use, hub 410 is initially disposed in a first rotational position, wherein first hollow compartment 416a is positioned adjacent contact pin opening 357 of housing 352, thus permitting insertion of contact pin 322 therethrough and into engagement with electrical contact 372 of needle electrode assembly 350. The insertion of contact pin 322 into housing 352 also permits sufficient approximation of housing 312 of handle assembly 310 and housing 352 of needle electrode assembly 350 to permit mechanical engagement therebetween. Upon use, e.g., upon supply of cooling fluid to needle 370, flanges 414 of hub 410 are translated along track 424 of housing 352 and are rotationally loaded such that, upon disengagement of needle electrode assembly 350 and handle assembly 310 after use, hub 410 is rotated to the next, e.g., the second, rotational position. As can be appreciated, three uses of needle electrode assembly 305 are permitted: the first when hub 410 is disposed in the first rotational position (wherein first hollow compartment 416a is positioned adjacent contact pin opening 357 of housing 352), the second when hub 410 is disposed in the second rotational position (wherein second hollow compartment 416b is positioned adjacent contact pin opening 357 of housing 352), and the third when hub 410 is disposed in the third rotational position (wherein third hollow compartment 316c is positioned adjacent contact pin opening 357 of housing 352). However, once rotated to the fourth rotational position, the final, filled compartment 416d inhibits insertion of contact pin 322 into housing 352 and, thus, inhibits both electrical coupling and mechanical engagement of needle electrode assembly 350 and handle assembly 310 to one another. That is, once the fourth rotational position is reached, needle electrode assembly 350 is "spent" and is no longer usable.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
   a reusable component configured to connect to a source of fluid; and
   a limited-use component releasably engagable with the reusable component, the limited-use component configured to receive fluid from the reusable component, the limited-use component including a clocking mechanism configured to count each successive use of the limited-use component upon supply of fluid to the limited-use component, the clocking mechanism incrementally transitionable upon each successive count from at least one use state, wherein the clocking mechanism permits coupling of the reusable component and the limited-use component to one another, to a spent state, wherein the clocking mechanism inhibits coupling of the reusable component and the limited-use component to one another.

2. The surgical instrument according to claim 1, wherein, in the at least one use state, the clocking mechanism permits both mechanical engagement and electrical communication between the reusable component and the limited-use component, and wherein, in the spent state, the clocking mechanism inhibits both mechanical engagement and electrical communication between the reusable component and the limited-use component.

3. The surgical instrument according to claim 1, wherein the limited-use component is configured for a pre-determined plurality of uses, and wherein the clocking mechanism is incrementally transitionable from a plurality of use states, each corresponding to one of the pre-determined plurality of uses, to the spent state.

4. The surgical instrument according to claim 1, wherein the clocking mechanism includes a hub and a housing, the hub disposed within the housing and rotatably and longitudinally movable relative to the housing to incrementally transition the clocking mechanism from the at least one use state to the spent state.

5. The surgical instrument according to claim 1, wherein the clocking mechanism further includes indicia configured to display a condition of the limited-use component.

6. The surgical instrument according to claim 5, wherein the indicia displays a number of uses remaining for the limited-use component.

7. The surgical instrument according to claim 1, wherein the reusable component is a handle assembly.

8. The surgical instrument according to claim 7, wherein the limited-use component is an electrode assembly releasably engagable with the handle assembly.

9. A surgical instrument, comprising:
   a reusable component configured to connect to a source of fluid; and
   a limited-use component configured to supply energy to tissue, the limited-use component releasably engagable with the reusable component and configured to receive fluid from the reusable component when engaged therewith to cool the limited-use component, the limited-use component including a clocking mechanism configured to count each successive use of the limited-use component upon supply of fluid to the limited-use component, the clocking mechanism incrementally transitionable upon each successive count from at least one use state, wherein the clocking mechanism permits coupling of the reusable component and the limited-use component to one another, to a spent state, wherein the clocking mechanism inhibits coupling of the reusable component and the limited-use component to one another.

10. The surgical instrument according to claim 9, wherein, in the at least one use state, the clocking mechanism permits mechanical engagement between the reusable component and the limited-use component, and wherein, in the spent state, the clocking mechanism inhibits mechanical engagement between the reusable component and the limited-use component.

11. The surgical instrument according to claim 9, wherein, in the at least one use state, the clocking mechanism permits electrical communication between the reusable component and the limited-use component, and wherein, in the spent state, the clocking mechanism inhibits electrical communication between the reusable component and the limited-use component.

12. The surgical instrument according to claim 9, wherein the limited-use component is configured for a pre-determined plurality of uses, and wherein the clocking mechanism is incrementally transitionable from a plurality of use states, each corresponding to one of the pre-determined plurality of uses, to the spent state.

13. The surgical instrument according to claim 9, wherein the clocking mechanism includes a hub and a housing, the hub disposed within the housing and rotatably and longitudinally movable relative to the housing to incrementally transition the clocking mechanism from the at least one use state to the spent state.

14. The surgical instrument according to claim 9, wherein the clocking mechanism further includes indicia configured to display a condition of the limited-use component.

15. The surgical instrument according to claim 14, wherein the indicia displays a number of uses remaining for the limited-use component.

16. The surgical instrument according to claim 9, wherein the reusable component is a handle assembly.

17. The surgical instrument according to claim 16, wherein the limited-use component is an electrode assembly releasably engagable with the handle assembly.

* * * * *